United States Patent [19]

De Vroom et al.

[11] Patent Number: 6,107,481
[45] Date of Patent: Aug. 22, 2000

[54] DE-ESTERIFICATION PROCESS

[75] Inventors: Erik De Vroom, Leiden; Thomas Van Der Does, Delft, both of Netherlands

[73] Assignee: DSM N.V., Netherlands

[21] Appl. No.: 09/352,288

[22] Filed: Jul. 13, 1999

Related U.S. Application Data

[63] Continuation of application No. 09/051,189, filed as application No. PCT/EP96/04880, Nov. 6, 1996, Pat. No. 5,922,861.

[30] Foreign Application Priority Data

Nov. 6, 1995 [EP] European Pat. Off. .............. 95202992

[51] Int. Cl.$^7$ ..................... C07D 499/00; C07D 501/02
[52] U.S. Cl. ..................... 540/304; 540/222; 540/225; 540/227; 540/228
[58] Field of Search ..................... 540/304, 225, 540/227, 228, 222

[56] References Cited

U.S. PATENT DOCUMENTS 4,985,554   1/1991   Verweig et al. ..................... 540/215
5,922,861   7/1999   De Vroom et al. ..................... 540/304

*Primary Examiner*—John M. Ford
*Assistant Examiner*—Pavanaram K. Sripada
*Attorney, Agent, or Firm*—Bierman, Muserlian and Lucas

[57] ABSTRACT

A process to prepare the E isomer of a 3-substituted (6R, 7R)-7-phenyl-acetamido-ceph-3-em-4-carboxylic acid from a mixture of the E and Z-isomer of either the corresponding tert-butyl or the corresponding 4-methoxybenzyl ester of a 3-substituted (6R,7R)-7-phenylacetamido-ceph-3-em-4-carboxylate, characterized by the application of a compound selected from the group titanium tetrachloride, tin tetrachloride and tellurium tetrachloride.

2 Claims, No Drawings

DE-ESTERIFICATION PROCESS

PRIOR APPLICATION

This application is a continuation of U.S. patent application Ser. No. 09/051,189 filed Apr. 1, 1998, now U.S. Pat. No. 5,922,861 which is a 371 filing of PCT Application PCT/EP96/04880 filed Nov. 6, 1996.

TECHNICAL FIELD

The present invention relates to an improved method for ester hydrolysis. In particular, the invention relates to the deprotection of carboxyl esters by reaction with acidic metal halogenides (Lewis acids).

BACKGROUND AND RELEVANT LITERATURE

The protection and deprotection of carboxyl esters is an important part of many syntheses wherein carboxylate groups are involved. For instance, this protection and deprotection does often play a role in the synthesis of semi-synthetic cephalosporins (SSC's) and semi-synthetic penicillins (SSP's). SSC's are derivatized congeners of 7-aminocephalosporanic acid (7-ACA) or 7-aminodesacetoxycephalosporanic acid (7-ADCA) and salts and esters thereof; SSP's are derivatized congeners of 6-aminopenicillanic acid (6-APA).

In synthetic schemes leading to SSC's and SSP's a variety of protecting groups is often employed. An important feature in protecting group strategy usually is blocking and deblocking of the carboxyl function since said carboxyl functions can undergo decarboxylation if left unreacted (*J. Amer. Chem. Soc.* 1969, 91, 1401). Protection is achieved using esterification with an alcohol that can be removed under acidic or neutral conditions. Important industrial examples of 4-carboxyl protecting groups are allyl, benzhydryl, benzyl, tert-butyl, 4-methoxybenzyl, 4-nitrobenzyl and trichloroethyl. The known methods for removal of protecting groups are either expensive (trifluoroacetic acid), difficult to process because of complexation (zinc/acetic acid), or suffer from low yields (hydrogenolysis in case of benzhydryl and benzyl).

It is accordingly an object of the present invention to provide a new and improved process for converting carboxyl esters to the corresponding acid in high yield without the production of unwanted by-products.

It is also an object of the invention to provide new compounds by the application of this process, as for instance (6R,7R)-3-(2,4-dinitrostyryl)-7-phenylacetamido-ceph-3-em-4-carboxylic acid (cefesone), and the conversion in salts and esters thereof, and the E-isomers of the same. The chemical name of the racemic mixture has recently been indicated in *J. Clin. Micr.* 1995, 1665, but a process to prepare the same has not been published up to now.

Aluminum trichloride-promoted hydrolysis of cephalosporin esters is a procedure reported for the hydrolysis of benzyl esters (*Tetrahedron Lett.* 1979, 2793), benzhydryl esters (*Pure & Appl. Chem.* 1987, 59, 1041), and 4-methoxybenzyl esters (*Pure & Appl. Chem.* 1989, 61, 325).

Surprisingly, it has been found that other Lewis acids, like tellurium tetrachloride, tin tetrachloride or titanium tetrachloride, can be applied for the high yield hydrolysis of carboxyl esters, such as tert-butyl and 4-methoxybenzyl.

SUMMARY OF THE INVENTION

The present invention provides a method for the hydrolysis of a carboxy-protected ester by reacting said ester with a compound selected from the group consisting of the tetrahalogenides of titanium, tin and tellurium.

Especially, the process of the present invention can be applied advantageously for the hydrolysis of β-lactam esters of general formula (I) to give corresponding cephalosporin or penicillin derivatives of formula (II) as depicted in the scheme below. In particular, the esters are tert-butyl and 4-methoxybenzyl esters. The Lewis acid is selected from the group consisting of tellurium tetrahalogenide, tin tetrahalogenide and titanium tetrahalogenide.

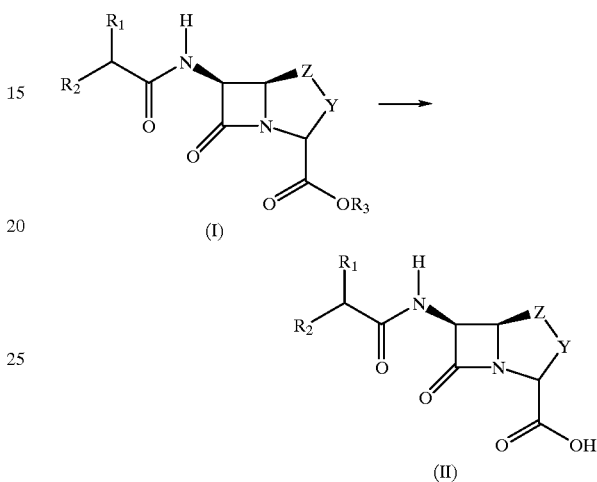

with $R_1$ is hydrogen, hydroxy, amine, halogen or lower alkyl;

$R_2$ is an optionally substituted phenyl or phenoxy or 5- or 6-membered heterocyclic ring;

$R_3$ is a carboxy-protecting group;

Z is oxygen, sulphur (optionally oxidized to sulfoxide or sulfone) or $CHR_5$ with $R_5$ is hydrogen or lower alkyl; and Y is

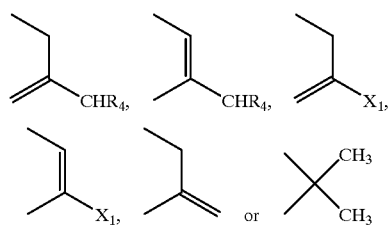

with $R_4$ is optionally substituted alkylidene; and $X_1$ is hydrogen, halogen or (lower) alkoxy or optionally substituted methyl or alkoxycarbonyl.

According to another aspect of this invention, the novel compound(6R,7R)-3-(2,4-dinitrostyryl)-7-phenylacetamido-ceph-3-em-4-carboxylic acid and salts and esters thereof, especially the E-isomer, has been provided for.

SPECIFIC EMBODIMENTS

According to the present invention, a process is provided for deesterification of carboxylate esters, for instance resulting in the preparation of 7-acylacetamido-cephem-4-carboxylic acids, 7-acylacetamido-cepham-4-carboxylic acids or 6-aminopenicillanic acid and pharmaceutically acceptable salts thereof of formula (II), starting from the corresponding esters of formula (I). The deesterification usually will be carried out in an organic solvent at a temperature of about −10° C.–20° C., preferably of about −5° C.–5° C.

The group $R_1$ can be optionally protected amino, halogen, hydrogen, optionally protected hydroxy or lower alkyl. Preferably $R_1$ is hydrogen.

The acylamido group $R_2$ can be any group hitherto disclosed in the chemical literature and patent specifications or known to those skilled in the art of cephalosporin and penicillin chemistry. Preferably $R_2$ is one present in the 6β-side chain of penicillins that can be obtained by fermentative procedures. The latter penicillins can be converted into cephalosporins by known methods. Suitable groups represented by $R_2$ are, for example, phenoxyacetamido, phenylacetamido and 2-thienylacetamido.

The group $R_3$ can be any group known to those skilled in the art for protecting the carboxy group of cephalosporanic acid or penicillanic acid derivatives. Preferably $R_3$ represents an ester group which can be easily introduced. Particularly suitable ester groups are allyl, benzhydryl, benzyl, 2-bromoethyl, tert-butyl, 4-methoxybenzyl, methyl, 4-nitrobenzyl and 2,2,2-trichloroethyl.

The group $R_4$ can be a C1–C6 alkylidene group like propenyl, optionally substituted by substituents like an acyl or heterocyclic group, optionally substituted by for instance halogen, hydroxy or nitro groups.

Examples of β-lactam derivatives that may be produced by the process of this invention are intermediates for antibiotics such as cefamandole, cefatrizine, cefdinir, cefixime, cefmenoxime, cefpodoxime, cefprozil, cefroxadine, ceftibuten, ceftiofur, ceftizoxime, ceftriaxone, cefuroxime, cefuzonam, loracarbef, moxalactam, and also active compounds such as said antibiotics. Furthermore, using the process of this invention, β-lactamase indicating compounds such as cefesone and nitrocefin can be prepared.

The starting materials used in the present invention are prepared according to methods published earlier. 3-Alkenyl substituted cephem derivatives can be prepared as described in European patent applications 292,806 and 421,219, and German patent 2,249,165. 3-Acetoxymethyl-, 3-methyl- and 3-thiomethyl substituted cephem derivatives are prepared according to *Recl. Trav. Chim. Pays-Bas* 1993, 112, 66. 3-Methylene cepham derivatives are prepared according to U.S. Pat. No. 4,985,564.

Tert-butyl-(6R,7R)-3-(2,4-dinitrostyryl)-7-phenylacetamido-ceph-3-em-4-carboxylate can be prepared by reacting the corresponding (2-halo)-3-halomethyl-3-cephem compound, viz. tert-butyl-(1S,6R,7R)-(2-halo)-3-halomethyl-1-oxo-7-phenylacetamido-3-cephem-4-carboxylate, with a phosphine according to EP-B-0299587 followed by reduction using phosphorous trichloride and condensation with 2,4-dinitrobenzaldehyde.

METHODS OF ANALYSIS

HPLC Column: Chrompack Microsphere C18, 3 μm (100× 3.0 mm).

Solvent: 30% Acetonitrile and 1% tetrahydrofuran in 7 mM potassium dihydrogenphosphate, pH 2.6.

Flow: 1.2 ml.min$^{-1}$.

Detection: 254 nm.

Retention: 7-phenylacetamido-3-deacetoxycephaloporanic acid (3.70 min); (6R,7R)-7-phenylacetamido-3-[(E)-1-propenyl]-ceph-3-em-4-carboxylic acid (8.02 min); (6R,7R)-7-phenylacetamido-3-[(Z)-1-propenyl]-ceph-3-em-4-carboxylic acid (6.20 min).

IR: Infrared spectra were recorded on a Pye Unicam PU9714.

MS: Mass spectra were obtained with an AMD 402 mass spectrometer.

NMR: $^1$H NMR spectra were recorded on a Bruker AM 360 MHz instrument. Purities were determined with $^1$H NMR spectroscopy using an internal reference.

TLC: Thin layer chromatography was performed using Merck Kiesel-gel 60 $F_{254}$ plates as stationary phase and ethylacetate/toluene/acetic acid 4/3/2/1 as mobile phase.

EXAMPLE 1

Synthesis of (6R,7R)-3-methyl-7-phenylacetamido-ceph-3-em-4-carboxylic acid

A stirred solution of tert-butyl (6R,7R)-3-methyl-7-phenyl-acetamido-ceph-3-em-4-carboxylate (0.873 g, purity 89%, 2.0 mmol) in dichloromethane (50 ml) was cooled to −20° C. Titanium tetrachloride (0.88 ml, 7.9 mmol) was added in 1 min. After stirring for 2 h at 0° C., the suspension was mixed with a chilled 2 M solution of hydrochloric acid in water (40 ml). The organic phase was separated and water was added. The pH was adjusted to 7.0 with a 2 M solution of sodium hydroxide in water and the aqueous phase was separated and the pH was adjusted to 2.0 with a 2 M solution of hydrochloric acid in water. A white product precipitated which was isolated and dried to give 0.49 g of (6R,7R)-3-methyl-7-phenylacetamido-ceph-3-em-4-carboxylic acid (purity 94%, yield 69.4%).

IR (KBr): 3270 cm$^{-1}$, 1770 cm$^{-1}$, 1700 cm$^{-1}$, 1655 cm$^{-1}$, 1550 cm$^{-1}$. $^1$H NMR (DMSO-d$_6$; 360 MHz): δ=2.03 (s, 3 H), 3.35/3.54 (ABq, 2 H, J=16.7 Hz), 3.55/3.62 (ABq, 2 H), 5.05 (d, 1 H, J=5.0 Hz), 5.60 (dd, 1 H), 7.3 (m, 5 H), 9.07 (d, 1 H, J=6.9 Hz) ppm.

EXAMPLE 2

Synthesis of (4R,6R,7R)-3-methylene-7-phenylacetamido-cepham-4-carboxylic acid

A stirred solution of tert-butyl (4R,6R,7R)-3-methylene-7-phenylacetamido-cepham-4-carboxylate (0.83 g, purity 93.7%, 2.0 mmol) in dichloromethane (80 ml) was cooled to 0° C. Titanium tetrachloride (0.66 ml, 6.0 mmol) was added in 1 min. After stirring for 4 h at 0° C., the suspension was mixed with a chilled 2 M solution of hydrochloric acid in. water (40 ml). The organic phase was separated and washed with a 1 M solution of hydrochloric acid in water (20 ml), water (20 ml), and brine (20 ml). The organic phase was dried over magnesium sulphate and evaporated to give 0.40 g of (4R,6R,7R)-3-methylene-7-phenylacetamido-cepham-4-carboxylic acid (purity 75%, yield 45.1%).

IR (KBr): 3280 cm$^{-1}$, 1745 cm$^{-1}$, 1635 cm$^{-1}$. $^1$H NMR (CDCl$_3$; 360 MHz): δ=3.17 (d, 1 H, J=15.0 Hz), 3.56/3.68 (m, 3 H), 5.07 (s, 1 H), 5.23 (ABq, 2H, J=12.5 Hz), 5.64 (dd, 1 H), 6.29 (d, 1H, J=11.0 Hz), 7.3 (m, 5 H).

EXAMPLE 3

Synthesis of (4R,6R,7R)-3-methyl-7-phenylacetamido-ceph-2-em-4-carboxylic acid

A stirred solution of tert-butyl (4R,6R,7R)-3-methyl-7-phenylacetamido-ceph-2-em-4-carboxylate (0.776 g, 2.0 mmol) in dichloromethane (30 ml) was cooled to 0° C.

Titanium tetrachloride (0.6 ml, 5.5 mmol) was added in 1 min. After stirring for 2.5 h at 0° C., the suspension was mixed with a chilled 2 M solution of hydrochloric acid in water (40 ml). The organic phase was separated and washed with a 1 M solution of hydrochloric acid in water (20 ml), water (20 ml), and brine (20 ml). The organic phase was concentrated to give 0.55 g of (4R,6R,7R)-3-methyl-7-phenylacetamido-ceph-2-em-4-carboxylic acid (yield 82.7%).

EXAMPLE 4

Synthesis of (6R,7R)-3-methyl-7-phenoxyacetamido-ceph-3-em-4-carboxylic acid A stirred solution of tert-butyl (6R,7R)-3-methyl-7-phenoxyacetamido-ceph-3-em-4-carboxylate (0.41 g, 1.0 mmol) in dichloromethane (25 ml) was cooled to 0° C. Titanium tetrachloride (0.38 ml, 3.5 mmol) was added in 1 min. A yellow precipitate was formed which was stirred for 2 h at 0° C. To the suspension was added a chilled 1 M solution of hydrochloric acid in water (40 ml). The organic phase was separated, washed with water and brine, dried over magnesium sulphate, and evaporated to give 0.30 g of (6R,7R)-3-methyl-7-phenoxyacetamidoceph-3-em-4-carboxylic acid (purity 63%, yield 54.3%).

IR (KBr): 3375 cm$^{-1}$, 1755 cm$^{-1}$, 1740 cm$^{-1}$, 1655 cm$^{-1}$.
$^1$H NMR (DMSO-d$_6$; 360 MHz): δ=2.06 (s, 3 H), 3.42/3.47 (ABq, 2 H, J=8.3 Hz), 3.59/3.64 (ABq, 2 H, J=16.6 Hz), 5.08 (d, 1 H), 5.66 (dd, 1 H), 6.3 (m, 5 H), 9.02 (d, 1 H, J=9.9 Hz) ppm.

EXAMPLE 5

Synthesis of (6R,7R)-7-phenylacetamido-3-(1-propenyl)-ceph-3-em-4-carboxylic acid, Z-isomer A stirred solution of 4-methoxybenzyl (6-R,7R)-7-phenylacetamido-3-(1-propenyl)-ceph-3-em-4-carboxylate (0.509 g, purity 9% E-isomer, 84% Z-isomer, 0.99 mmol) in dichloromethane (15 ml) was cooled to 2° C. Titanium tetrachloride (0.5 ml, 4.5 mmol) was added in 1 min. After 30 min the brown suspension was mixed with a chilled mixture of dichloromethane (50 ml) and a 2 M solution of hydrochloric acid in water (50 ml). The organic phase was separated and extracted with a 2 M solution of hydrochloric acid in water (3×50 ml) The aqueous phases were extracted with dichloromethane (25 ml). The combined organic phases were analyzed using HPLC: 0.036 g (6R,7R)-7-phenylacetamido-3-[(E)-1-propenyl]-ceph-3-em-4-carboxylic acid (0.10 mmol, yield 10.2%); 0.301 g (6R,7R)-7-phenylacetamido-3-[(Z)-1-propenyl]-ceph-3-em-4-carboxylic acid (0.84 mmol, yield 84.8%). The overall yield is therefore 95.0%.

EXAMPLE 6

Screening of lewis acids in the hydrolysis of tert-butyl (6R,7R)-7-phenyl-acetamido-3-(1-propenyl)-ceph-3-em-4-carboxylate To a stirred solution of tert-butyl (6R,7R)-7-phenylacetamido-3-(1-propenyl)-ceph-3-em-4-carboxylate in dichloromethane (30 ml.g$^{-1}$) was added Lewis acid (3–5 equiv., see table for conditions). The formation of (6R,7R)-7-phenylacetamido-3-(1-propenyl)-ceph-3-em-4-carboxylic acid was monitored either by HPLC or TLC. The results are summarized in the table.

| Lewis acid | T (° C.) | Time (h) | Yield (%) | Remarks |
|---|---|---|---|---|
| AlCl$_3$ | 25 | 28 | 50 | According to TLC; some degradation observed. |
| BCl$_3$ | -10 | 4 | 20 | According to TLC; extensive degradation observed. |
| BF$_3$ | 25 | 18 | 0 | According to TLC; no product, no starting material. |
| FeCl$_3$ | 5 | 2.5 | 34 | According to HPLC; yield after work-up. |
| SiCl$_4$ | 25 | 72 | 0 | According to TLC; no reaction observed. |
| SnCl$_4$ | -10 | 2.5 | 88 | According tb HPLC; tin-residues are difficult to remove during work-up. |
| TiCl$_4$ | 5 | 3 | 91 | According to HPLC. |

EXAMPLE 7

Synthesis of (1S,6R,7R)-3-acetoxymethyl-1-oxo-7-phenylacetamido-ceph-3-em-4-carboxylic acid To a stirred solution of tert-butyl (1S,6B,7R)-3-acetoxymethyl-1-oxo-7-phenylacetamido-ceph-3-em-4-carboxylate (0.23 g, purity 89.3%, 0.423 mmol) in acetonitrile (2.5 ml) was added a solution of tellurium tetrachloride (0.135 g, 0.5 mmol) in acetonitrile (2.5 ml). After stirring for 1 h at 23° C., the crystalline precipitate was collected by filtration, washed with acetonitrile (0.5 ml) and dried over phosphorous pentachloride under vacuum to give 0.147 g of (1S,6R,7R)-3-acetoxymethyl-1-oxo-7-phenylacetamido-ceph-3-em-4-carboxylic acid (purity 87%, 75.1% yield). The filtrate was treated with ether (10 ml) to give a second crop of product (0.008 g, purity 82%, 3.9% yield). The total yield is 79.0%.

EXAMPLE 8

Synthesis of (6R,7R)-7-phenylacetamido-3-(1-propenyl)-ceph-3-em-4-carboxylic acid, Z-isomer At 0° C., titanium tetrachloride (420 ml, 3.82 mol) was added in 30 min to a solution of tert-butyl (6R,7R)-7-phenylacetamido-3-(1-propenyl)-ceph-3-em-4-carboxylate, (404.8 g, 976.5 mmol; ratio E-isomer:Z-isomer=0.05). After stirring for 1 h at 1±1°0 C., the solution is transferred to a stirred 2 M solution of hydrochloric acid in water (6.00 l). The layers are separated and the aqueous phase was back-extracted with dichloromethane (800 ml). The combined organic phases were extracted with a 2 M solution of hydrochloric acid in water (3×31) and each batch of water was back-extracted with the wash-dichloromethane. The combined organic phases (6.03 l) were analyzed using HPLC: 16.9 g(6R,7R)-7-phenylacetamido-3-[(E)-1-propenyl]-ceph-3-em-4-carboxylic acid (47.2 mmol, yield 4.8%); 296.1 g (6R,7R)-7-phenylacetamido-3-[(Z)-1-propenyl]-ceph-3-em-4-carboxylic acid (826.1 mmol, yield 84.6%). The overall yield is therefore 89.4%.

EXAMPLE 9

Synthesis of (6R,7R)-3-(2,4-dinitrostyryl)-7-phenylacetamido-ceph-3-em-4-carboxylic acid, E-isomer A stirred solution of tert-butyl (6R,7R)-3-(2,4-dinitrostyryl)-7-phenylacetamido-ceph-3-em-4-carboxylate (67.41 g, purity 8% E-isomer, 81% Z-isomer, 105.9 mmol)

in dichloromethane (1685 ml) was cooled to −25° C. Titanium tetrachloride (53 ml, 482 mmol) was added in 10 min and the temperature was brought to 0° C. After 105 min a chilled 2 M solution of hydrochloric acid in water was added at such a rate that the temperature remained under 10° C. The organic phase was separated and extracted with a 2 M solution of hydrochloric acid in water (2×1685 ml) and brine (1685 ml). The organic phase was concentrated under reduced pressure to give an orange foam. Crude product thus obtained was crystallized by dissolving in acetone (1350 ml) at 65° C. and adding water (675 ml). Crystallization was allowed to proceed for 16 h at 0° C. and the crystals were collected by filtration. Recrystallization of the product was performed by dissolving the material in acetone/acetic acid (2:1) at 53° C., removing solvent (1700 ml) by evaporation under reduced pressure and stirring for 16 h at 20° C. Crystals were collected by filtration, washed with acetic acid (300 ml) and ether (250 ml), and dried under vacuum at 45° C. to give 34.33 g (purity 99% E-isomer, 66.6 mmol; yield 63%) of (6R,7R)-3-(2,4-dinitrostyryl)-7-phenylacetamido-ceph-3-em-4-carboxylic acid as yellow crystals.

IR (KBr): 3300 cm$^{-1}$, 1780 cm$^{-1}$, 1715 cm$^{-1}$, 1625 cm$^{-1}$, 1525 cm$^{-1}$. MS (DCI): m/z=528.0 (MNH$_4^+$). $^1$H NMR (CDCl$_3$/DMSO-d$_6$, 1:2; 360 MHz): δ=3.50/3.58 (ABq, 2 H, J=14.1 Hz), 3.62/3.77 (ABq, 2 H. J=17.5 Hz), 5.05 (d, 1 H, J=4.9 Hz), 5.72 (dd, 1 H, J$_{6,7}$=4.9 Hz, J$_{7,NH}$=8.3 Hz), 7.3 (m, 6 H), 7.63 (d, 1 H, J=16.1 Hz), 7.82 (d, 1 H, J=8.8 Hz), 8.33 (dd, 1 H, J$_1$=2.1 Hz, J$_2$=8.8 Hz), 8.66 (d, 1 H, J=2.1 Hz), 8.97 (d, 1 H, J=8.3 Hz) ppm.

EXAMPLE 10

Synthesis of (6R,7R)-7-phenylacetamido-3-(1-phenyl-1-H-tetrazol-5-yl)thiomethyl-ceph-3-em-4-carboxylic acid A stirred solution of tert-butyl (6R,7R)-7-phenylacetamido-3-(1-phenyl-1-H-tetrazol-5-yl)thiomethyl-ceph-3-em-4-carboxylate (1.0 g, purity 80%, 1.42 mmol) in dichloromethane (50 ml) was cooled to 0° C. Titanium tetrachloride (0.62 ml, 5.6 mmol) was added in 1 min. After stirring for 1 h at 0° C., the suspension was mixed with a chilled 2 M solution of hydrochloric acid in water (40 ml). The organic phase was separated and washed with a 1 M solution of hydrochloric acid in water (20 ml), water (20 ml), and brine (20 ml). The organic phase was dried over magnesium sulphate and evaporated to give 0.55 g of (6R,7R)-7-phenylacetamido-3-(1-phenyl-1-H-tetrazol-5-yl)thiomethyl-ceph-3-em-4-carboxylic acid-(purity 60%, yield 45.8%).

IR (KBr): 3260 cm$^{-1}$, 1770 cm$^{-1}$, 1485 cm$^{-1}$. $^1$H NMR (DMSO-d$_6$; 360 MHz): δ=1.25 (s, 2H), 3.47/3.65 (m, 2 H), 3.68 (ABq, 2H, J=11.7 Hz), 4.28 (d, 1H, J=13.3 Hz), 4.56 (d, 1H, J=13.3 Hz), 5.04 (d, 2H, J=6.1 Hz), 5.71 (m, 2H), 7.01 (m, 1H), 7.2/7.8 (m, 10 H), 9.14 (d, 1H, J=11.5 Hz).

EXAMPLE 11

Synthesis of (6R,7R)-7-phenylacetamido-3-(1-phenyl-1-H-tetrazol-5-yl)thiomethyl-ceph-3-em-4-carboxylic acid A stirred solution of tert-butyl (6R,7R)-7-phenylacetamido-3-(1-phenyl-1-H-tetrazol-5-yl)thiomethyl-ceph-3-em-4-carboxylate (1.0 g, purity 80%, 1.42 mmol) in dichloromethane (50 ml) and anisole (0.93 ml) was cooled to 0° C. Titanium tetrachloride (0.62 ml, 5.6 mmol) was added in 1 min. After stirring for 2.5 h at 0° C., the suspension was mixed with a chilled 2 M solution of hydrochloric acid in water (40 ml). The organic phase was separated and washed with a 1 M solution of hydrochloric acid in water (20 ml), water (20 ml), and brine (20 ml). The organic phase was dried over magnesium sulphate and evaporated to give 0.60 g of (6R,7R)-7-phenylacetamido-3-(1-phenyl-1-H-tetrazol-5-yl)thiomethyl-ceph-3-em-4-carboxylic acid (purity 60%, yield 49.9%).

IR (KBr): 3260 cm$^{-1}$, 1770 cm$^{-1}$, 1485 cm$^{-1}$. $^1$H NMR (DMSO$_6$; 360 MHz): δ=1.25 (s, 2H), 3.47/3.65 (m, 2 H), 3.68 (ABq, 2H, J=11.7 Hz), 4.28 (d, 1H, J=13.3 Hz), 4.56 (d, 1H, J=13.3 Hz), 5.04 (d, 2H, J=6.1 Hz), 5.71 (m, 2H), 7.01 (m, 1H), 7.2/7.8 (m, 10 H), 9.14 (d, 1H, J=11.5 Hz).

EXAMPLE 12

Synthesis of (6R,7R)-7-phenylacetamido-3-(1-phenyl-1-H-tetrazol-5-yl)thiomethyl-ceph-3-em-4-carboxylic acid A stirred solution of tert-butyl (6R,7R)-7-phenylacetamido-3-(1-phenyl-1-H-tetrazol-5-yl)thiomethyl-ceph-3-em-4-carboxylate (5.0 g, purity 80%, 7.09 mmol) in dichloromethane (150 ml) was cooled to 0° C. A solution of titanium tetrachloride (2.33 ml, 21.2 mmol) in dichloromethane (15 ml) was added. After stirring for 4.5 h at 0° C., the suspension was mixed with a chilled 2 M solution of hydrochloric acid in water. The organic phase was separated and washed with a 1 M solution of hydrochloric acid in water, water, and brine. The organic phase was dried over magnesium sulphate and concentrated to give 3.55 g of (6R,7R)-7-phenylacetamido-3-(1-phenyl-1-H-tetrazol-5-yl)thiomethyl-ceph-3-em-4-carboxylic acid (purity 60%, yield 59.1%).

IR (KBr): 3260 cm$^{-1}$, 1770 cm$^{-1}$, 1485 cm$^{-1}$. $^1$H NMR (DMSO$_6$; 360 MHz): δ=1.25 (s, 2H), 3.47/3.65 (m, 2 H), 3.68 (ABq, 2H, J=11.7 Hz), 4.28 (d, 1H, J=13.3 Hz), 4.56 (d, 1H, J=13.3 Hz), 5.04 (d, 2H, J=6.1 Hz), 5.71 (m, 2H), 7.01 (m, 1H), 7.2/7.8 (m, 10 H), 9.14 (d, 1H, J=11.5 Hz).

EXAMPLE 13

Synthesis of (6R,7R)-7-phenylacetamido-3-(pyrimidin-2-yl) thiomethyl-ceph-3-em-4-carboxylic acid A stirred solution of tert-butyl (6R,7R)-7-phenylacetamido-3-(pyrimidin-2-yl)thiomethyl-ceph-3-em-4-carboxylate (3.5 g, purity 53%, 3.71 mmol) in dichloromethane (150 ml) and anisole (4.65 ml) was cooled to O° C. A solution of titanium tetrachloride (2.3 ml, 21 mmol) in dichloromethane (10 ml) was added. After stirring for 3.5 h at 0° C., the suspension was mixed with a chilled 2 M solution of hydrochloric acid in water. The organic phase was separated and washed with a 1 M solution of hydrochloric acid in water, water, and brine. The organic phase was dried over magnesium sulphate and concentrated to give 2.10 g of (6R,7R)-7-phenylacetamido-3-(pyrimidin-2-yl)thiomethyl-ceph-3-em-4-carboxylic acid (purity 75%, yield 50.9%).

IR (KBr): 3240 cm$^{-1}$, 1760 cm$^{-1}$, 1695 cm$^{-1}$, 1640 cm$^{-1}$, 1525 cm$^{-1}$. $^1$H NMR (DMSO$_6$; 360 MHz): δ=2.52 (s, 1H), 3.47/3.64 (ABq, 2 H, J=12.5 Hz), 3.75/4.02 (m, 2H), 4.60 (d, 1H, J=15.0 Hz), 5.08 (d, 1H, J=5.0 Hz), 5.62 (ABq, 1H, J=5.0 Hz), 7.28 (m, 6H), 8.68 (d, 2H, J=3.4 Hz), 9.15 (d, 1H, J=10.0 Hz).

We claim:

1. A process to prepare the E isomer of a 3-substituted (6R,7R)-7-phenyl-acetamido-ceph-3-em-4-carboxylic acid from a mixture of the E and Z-isomer of either the corresponding tert-butyl or the corresponding 4-methoxybenzyl ester of a 3-substituted (6R,7R)-7-phenylacetamido-ceph-3-em-4-carboxylate, characterized by the application of a compound selected from the group titanium tetrachloride, tin tetrachloride and tellurium tetrachloride.

2. A process according to claim 1, characterized by the preparation of the E-isomer of (6R,7R)-3-(2,4-dinitrostyryl)-7-phenylacetamido-ceph-3-em-4-carboxylic acid from a mixture of the E and Z-isomer of the tert-butyl ester of (6R,7R)-3-(2,4-dinitrostyryl)-7-phenylacetamido-ceph-3-em-4-carboxylic acid.

* * * * *